US008828450B2

(12) United States Patent
Pujos et al.

(10) Patent No.: US 8,828,450 B2
(45) Date of Patent: Sep. 9, 2014

(54) COMPOSITIONS FOR USE AGAINST ONE OR MORE PATHOGENS

(75) Inventors: Philippe Pujos, Lille (FR); Mohamed Haïssam Jijakli, Brussels (BE)

(73) Assignee: Bionext, Rixensart (Rosieres) (BE)

( * ) Notice: Subject to any disclaimer, the term of this patent is extended or adjusted under 35 U.S.C. 154(b) by 1082 days.

(21) Appl. No.: 11/663,641

(22) PCT Filed: Sep. 23, 2005

(86) PCT No.: PCT/EP2005/010342
§ 371 (c)(1),
(2), (4) Date: Oct. 3, 2007

(87) PCT Pub. No.: WO2006/032530
PCT Pub. Date: Mar. 30, 2006

(65) Prior Publication Data
US 2008/0160101 A1   Jul. 3, 2008

(30) Foreign Application Priority Data
Sep. 24, 2004   (EP) ..................................... 04447209

(51) Int. Cl.
*A61K 31/70* (2006.01)
*A61K 31/19* (2006.01)
*A61K 31/366* (2006.01)
*A01N 37/36* (2006.01)

(52) U.S. Cl.
CPC ..................................... *A01N 37/36* (2013.01)
USPC ............ 424/602; 514/23; 514/460; 424/93.1; 424/93.51; 424/611

(58) Field of Classification Search
CPC ... A01N 37/36; A01N 2300/00; A01N 63/00; A01N 63/04; A01N 65/00; A01N 65/08; A01N 65/34; A01N 65/38; C12N 1/00; C12R 1/66; C12R 1/80; C12R 1/645
USPC ............ 514/23, 474, 460, 557, 574; 424/602, 424/93.1, 93.51, 611
See application file for complete search history.

(56) References Cited

U.S. PATENT DOCUMENTS

| | | | |
|---|---|---|---|
| 3,639,631 A * | 2/1972 | Badcock et al. | ............... 514/636 |
| 4,818,530 A | 4/1989 | Marois et al. | |
| 5,591,429 A * | 1/1997 | Wilson et al. | ............... 424/93.51 |
| 5,780,023 A | 7/1998 | McLaughlin et al. | |
| 6,423,310 B1 * | 7/2002 | Wilson et al. | ............... 424/93.51 |

FOREIGN PATENT DOCUMENTS

| | | |
|---|---|---|
| DE | 19932055 A1 | 1/2001 |
| EP | 1 238 587 A | 9/2002 |
| JP | 03-213112 B2 | 10/2001 |
| WO | WO 96/28022 A | 9/1996 |
| WO | WO 00/44230 A | 8/2000 |

OTHER PUBLICATIONS

Palou et al., Evaluation of food additives and low-toxicity compounds as alternative chemicals for the control of *Penicillium digitatum* and *Penicillium italicum* on citrus fruit, Pest Management Science, 2002 vol. 58 No. 5 pp. 459-466.*
Droby et al. (abstract only, phytopathology, Apr. 2002, vol. 92 (4) pp. 393-399.*
Lahlali et al. (Biological control 51, 2009 pp. 403-408.*
Karasevicz (plant diseases, cornell edu. 1995, downloaded from the internet on Dec. 6, 2013, url: http://www.gardening.cornell.edu/education/mgprogram/mgmanual/04diseases.pdf.*
M. Shankar et al., "Nutritional and environmental factors affecting growth and antifungal activity of a sterile red fungus against *Gaeumannomyces graminis* var. *tritici*", Biosciences Information Service and Canadian Journal of Botany, 1994, p. 198-202, vol. 72, No. 2, XP002328037 abstract.
Cho, C.T., et al, "Biological Control of *Fusarium-oxysporum*-F-Sp-*Cucumerinum* Causing Cucumber Wilt by *Gliocladium*-Virens and *Trichoderma harzianum*", Biosciences Information Service, Philadelphia, PA., U.S., 1989, XP002328036 and orean Journal of Plant Pathology, vol. 5, No. 3, 1989, pp. 239-249.
European Search Report, May 12, 2005.
International Search report, Feb. 3, 2006.
Derwent Abstract for JP 03-213112, Oct. 2, 2001, XP002328038.

* cited by examiner

*Primary Examiner* — Savitha Rao
(74) *Attorney, Agent, or Firm* — Sughrue Mion, PLLC

(57) ABSTRACT

The present invention relates to a composition for use against one or more pathogens, comprising at least one antagonistic micro-organism and at least one salt and/or derivatives thereof as defined in claim 1. The present invention further relates to said composition for use as biopesticide.

19 Claims, No Drawings

COMPOSITIONS FOR USE AGAINST ONE OR MORE PATHOGENS

FIELD OF THE INVENTION

The present invention relates to compositions containing antagonistic micro-organisms and salts. The present invention further relates to said composition for use as biopesticide.

BACKGROUND OF THE INVENTION

Pathogenic infections, such as fungal infections, of animals including humans and plants produce significant losses in productive capacity worldwide. A great number of pathogens are responsible of important economical losses in crops and harvested products. For instance, *Penicillium* and *Botrytis* species are responsible for important economical losses. The common occurrence of these species in food is a particular problem. Some species produce toxins and may render food inedible or even dangerous. Species of *Penicillium* can cause severe fruit rot for example on apples (*Malus*), pears (*Pyrus*) and lemon (*Citrus* spp).

Pesticides against pathogens are well known in the art and have been intensively used for many years. Methods for the prophylactic and/or therapeutic treatment of fungal and bacterial infections in animals and plants generally involve the application of anti-fungal and anti-bacterial agrochemical products or the use of more environment-friendly biopesticides based on biocontrol agents. The interest for biological control over chemical control is rapidly growing for some reasons, such as residual reduction, environmental concerns, apparition of pathogen strains resistant to chemical pesticides or limitation of use of chemical pesticides.

As biocontrol agents, micro-organisms that are antagonistic to pathogens are known. Documents which relate to the use of compositions comprising yeast's or other micro-organisms against plant pathogens have been published, amongst which EP 1 238 587 which discloses in its examples composition comprising an antagonistic microorganism with high concentration of $CaCl_2$ 2% (20 g/l). WO 99/62340, WO 99/62341, U.S. Pat. No. 5,525,132, U.S. Pat. No. 5,741,699, U.S. Pat. No. 6,060,429, WO 00/44230, U.S. Pat. No. 5,288,488 and U.S. Pat. No. 5,780,023 may be cited as other examples.

Various micro-organisms amongst bacteria, fungi and yeast's have successfully been used against plant diseases caused by pathogens. Commercial biocontrol products such as Aspire™ (*Candida oleophila* Montrocher, 1-182) and Biosave™ (*Pseudomonas syringae* van Hall, Esc-11) was and are already available respectively from Ecogen Inc. (Longhorn, Pa.) and Ecoscience Corp. (Worcester, Mass.) and are used among others on postharvest apples against wound diseases.

However these biopesticides were often found not efficient enough. These first generation biocontrol products, relying on the use of single antagonists, have been criticized for not providing a stable and reliable protective activity when used under commercial conditions. To improve their natural ability to control fungi and particularly *Penicillium expansum* infections, reduce volume to handle, and costs, new stimulating agents have been searched.

Indeed, more efficient compositions enable to use lesser quantities of antagonistic micro-organisms per treatment, without lowering the efficiency of the composition against pathogens and without restricting the duration of the efficiency of the composition against pathogens, and, so, to reach the economical threshold of profitability.

In view of the foregoing, it is a main object of the present invention to provide novel compositions which are suitable for use against diseases caused to plants, product thereof and animals by pathogens, such as diseases induced by moulds. Another object of the present invention is to provide compositions that are at least as efficient as the ones of the state of the art. A further object of the invention is to provide compositions which comprise lower concentrations of antagonistic micro-organisms while having a similar or better efficiency against the pathogens.

SUMMARY OF THE INVENTION

In a first aspect, the present invention provides a novel composition suitable for use against one or more pathogens, comprising at least one antagonistic micro-organism and at least one calcium, sodium or potassium salt selected from the group comprising compound of formula (1), phosphate salts, sulphate salts, salts of ascorbic acid, isocitric acid, citramalic acid, lactogluconic acid, and/or derivatives thereof,

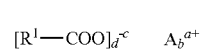
(1)

wherein
A is a cation selected from Ca, K or Na, preferably Ca or K, more preferably Ca, wherein a, b, c and d are integers from 1 to 3 with the proviso that a×b=c×d, and $R^1$ is selected from —O⁻, —OH or

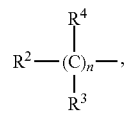

n is an integer from 0 to 5, $R^2$ is selected from H, —OH, —$CH_3$, —$CO_2^-$, —$CH_2$—OH, —$CH_2$—$CO_2^-$, $R^3$ is selected from H or —$CH_2$—COO⁻, and $R^4$ is selected from H, —$NH_2$ or OH, wherein when n is 1, if $R^4$ is H, $R^3$ is not H and $R^2$ is not —$CH_3$.

In particular, the present invention relates to a composition suitable for use against one or more pathogens, comprising at least one antagonistic micro-organism and at least one salt selected from calcium sulphate, calcium phosphate monobasic $Ca(H_2PO_4)_2$, calcium phosphate dibasic ($CaHPO_4$), calcium phosphate tribasic ($Ca_3(PO_4)_2$), calcium carbonate ($CaCO_3$), calcium bicarbonate ($Ca(HCO_3)_2$), calcium acetate, calcium ethanoate, calcium glycerate, calcium lactate, calcium glutamate, calcium erythronate, calcium theonate, calcium ribonate, calcium arabinoate, calcium xylonate, calcium lyxonate, calcium allonate, calcium altronate, calcium gluconate, calcium mannoate, calcium gulonate, calcium idonate, calcium galactonate, calcium talonate, calcium alloheptonate, calcium altroheptonate, calcium glucoheptonate, calcium mannoheptonate, calcium guloheptonate, calcium idoheptonate, calcium galactoheptonate, calcium taloheptonate, calcium tartronate, calcium malate, calcium tartrate, calcium citrate, calcium saccharate, calcium mucate, calcium lactogluconate, calcium ascorbate, calcium isocitrate, or calcium citramalate.

According to an embodiment of the present invention, said at least one antagonistic micro-organism is selected from the group comprising bacteria, fungus and yeast. In a particular embodiment, said antagonistic microorganism is selected from the group comprising *Agrobacterium* spp., *Ampelomyces* spp., *Aureobasidium* spp; *Bacillus* spp., *Bulleromyces* spp., *Candida* spp., *Chaetomium* spp., *Coniothyrium* spp., *Cryptococcus* spp., *Debaryomyces* spp., *Dekkera* spp., *Erwinia* spp., *Exophilia* spp., *Gliocladium* spp., *Hansenula* spp. *Issatchenkia* spp., *Kluyveromyces* spp., *Mariannaea* spp., *Metschnikovia* spp., *Microdochium* spp., *Penicillium* spp., *Phlebiopsis* spp.; *Pichia* spp., *Pseudomonas* spp., *Pseudozyma* spp., *Rhodotorula* spp., *Saccharomyces* spp., *Sporobolomyces* spp., *Streptomyces* sp., *Talaromyces* spp., *Trichoderma* spp., *Ulocladium* spp., *Zygosaccharomyces* spp., preferably *Agrobacterium radiobacter, Bacillus subtilis, Bacillus licheniformis, Bacillus pumilis, Candida oleophila, Candida saitoana, Candida sake, Candida tenius, Candida utilis, Coniothyrium minitans, Cryptococcus albidus, Erwinia carotovora, Gliocladium catenalatum, Gliocladium virens, Hanseniaspora uvarum, Kluyveromyces thermotolerance, Metschnikovia fructicola, Metschnikowia reukafii, Microdochium dimerum, Penicillium oxalicum, Phlebiopsis gigantean, Pichia anomala, Pichia guilliermondii, Pseudomonas cepacia, Pseudomonas chlororaphis, Pseudomonas fluorescens, Pseudomonas syringae, Pseudozyma flocullosa, Rhodotorula glutinis, Rhodotorula mucilaginosa, Saccharomyces cerevisiae, Streptomyces griseoviridis, Talaromyces flavus, Trichoderma atroviride, Trichoderma harzianum, Trichoderma polysporum, Trichoderma viride, Ulocladium atrum.*

In an embodiment of the present invention, the at least one salt to be used in the present composition is a calcium salt. In a preferred embodiment, the salt is calcium gluconate, calcium citrate, calcium carbonate, calcium lactate, calcium bicarbonate, calcium phosphate monobasic $Ca(H_2PO_4)_2$, calcium phosphate dibasic ($CaHPO_4$), calcium phosphate tribasic ($Ca_3(PO_4)_2$), calcium lactogluconate, calcium ascorbate.

The salt was found to have surprising enhancing properties on the biological activity of antagonistic micro-organisms. The association was particularly active even at low salts concentration i.e. below 5 g/l. The association was shown to be more effective than when using the micro-organism alone. For the same amount of salts, the present inventors have obtained a similar efficacy than when using high concentration of $CaCl_2$ 2% (20 g/l) together with the antagonistic microorganism. The composition according to the invention showed surprisingly very good efficacy at low dose of salt, i.e. below 5 g/l, and showed similar or better efficiency than composition with antagonistic microorganism comprising high concentration of $CaCl_2$ 2% (20 g/l). The present composition has an improved and/or longer efficacy against diseases caused by pathogens to plants and/or animals. The present composition is particularly effective for instance against diseases caused by moulds that colonize parts of plants, either after harvesting or during the plant life cycle.

The association was shown to be more effective than when using the micro-organism alone. The present composition permits the use of lower amounts of micro-organism and/or lower amounts of salts while having a similar or even better efficiency against the pathogens.

The present composition is useful against one or more pathogens that are able to cause diseases to plants or animals including humans. Said pathogen may be fungus, yeast, bacteria and viruses.

The composition according to the present invention is particularly useful against pathogens able to cause diseases to vegetal material. As used herein the term "plant" encompasses the whole plant, plants parts, fruits and other plant related material. Non limiting example of plants includes vegetal material which may be selected from the group comprising plant parts, fruits such as the species *Malus* spp., *Pyrus* spp., *Citrus* spp. (e.g., orange, lemon, grapefruit, tangerine), and crops such as the species tomato, bell pepper, cucumber, grapevine and strawberry); root crops (e.g., potato, carrots); tropical fruit (e.g., mango, banana, guava, pineapple, avocado); melon fruit, and flowers and other ornamental crops. The efficacy of the composition according to the invention is superior to that obtained with antagonistic microorganism alone at the same concentration and similar to that obtained with high concentration of $CaCl_2$ (2% w/v) with the microorganism.

The present invention also relates to a method for the biocontrol of diseases caused by pathogens to vegetal material, comprising the step of applying a composition according to the invention to said vegetal material.

The present invention further relates to the use of a composition according to the invention as a biopesticide, preferably as biofungicide, biovirucide and/or as a biobactericide, and to a method for the manufacture of a biopesticide comprising a composition according to the invention.

The present invention will be further disclosed in detail hereunder. Examples are given which will further support the description.

DETAILED DESCRIPTION

The present invention relates to compositions and methods for the control of fungal and bacterial plant pathogens. In particular, the present invention relates to a composition suitable for use against one or more pathogens comprising at least one antagonistic micro-organism and at least one calcium, sodium or potassium salt selected from the group comprising compound of formula (1); phosphate salts, sulphate salts, salts of ascorbic acid, isocitric acid, citramalic acid, lactogluconic acid and/or derivatives thereof and/or mixtures thereof,

 (1)

wherein
A is a cation selected from Ca, K or Na, preferably from Ca and K, more preferably from Ca.
a, b, c and d are integers from 1 to 3 with the proviso that a×b=c×d, and
$R^1$ is selected from —O⁻, —OH or

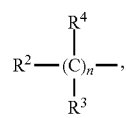

n is an integer from 0 to 5, $R^2$ is selected from H, —OH, —CH$_3$, —CO$_2^-$, —CH$_2$—OH, —CH$_2$—CO$_2^-$, $R^3$ is selected from H or —CH$_2$—COO⁻, and $R^4$ is selected from H, —NH$_2$ or OH, wherein when n is 1, if $R^4$ is H, $R^3$ is not H and $R^2$ is not —CH$_3$. It was surprisingly found that the combination of the composition gave control superior to that of the antagonistic micro-organism alone.

In a particular embodiment, the amount of the at least one salt is comprised between 0.005 and 5 g/l w/v, preferably between 0.01 and 4 g/l w/v, more preferably between 0.1 and 3 g/l w/v, more preferably between 0.01 and 2.5 g/l w/v, and yet more preferably between 0.1 and 2.2 g/l w/v. In another embodiment, said antagonistic micro-organism is applied at a concentration ranging from $10^3$ to $10^{111}$ cfu/ml, preferably from $10^4$ to $10^{10}$ cfu/ml. Another example of suitable concentration includes $10^6$ to $10^8$ cfu/ml and preferably the concentration of the micro-organism is from $10^6$ to $10^8$ cfu/ml, when said antagonistic microorganism is a fungus and $10^5$ to $10^{11}$, and preferably $10^9$ to $10^{11}$ when said antagonistic microorganism is a bacteria.

According to a preferred embodiment, said salt is selected from the group comprising of sulphate salt, phosphate salt, carbonate salt, bicarbonate salt, acetate salt, ethanoate salt, glycerate salt, glutamate salt, erythronate salt, theonate salt, ribonate salt, arabinoate salt, xylonate salt, lyxonate salt, allonate salt, altronate salt, gluconate salt, mannoate salt, gulonate salt, idonate salt, galactonate salt, talonate salt, alloheptonate salt, altroheptonate salt, glucoheptonate salt, mannoheptonate salt, guloheptonate salt, idoheptonate salt, galactoheptonate salt, taloheptonate salt, tartronate salt, malate salt, tartrate salt, citrate salt, saccharate salt, mucate salt, lactate salt, lactogluconate salt, ascorbate salt, isocitrate salt, and citramalate salt.

The salt may be under a hydrated form or anhydrous. The present composition may, of course, also contain mixtures of salts and/or polymers thereof.

In an embodiment of the present invention, the salt to be used in the present composition is a calcium salt.

According to a preferred embodiment, the salt is selected from the group comprising calcium sulphate, calcium phosphate monobasic $Ca(H_2PO_4)_2$, calcium phosphate dibasic ($CaHPO_4$), calcium phosphate tribasic ($Ca_3(PO_4)_2$), calcium carbonate ($CaCO_3$), calcium bicarbonate ($Ca(HCO_3)_2$), calcium acetate, calcium ethanoate, calcium glycerate, calcium glutamate, calcium erythronate, calcium theonate, calcium ribonate, calcium arabinoate, calcium xylonate, calcium lyxonate, calcium allonate, calcium altronate, calcium gluconate, calcium mannoate, calcium gulonate, calcium idonate, calcium galactonate, calcium talonate, calcium alloheptonate, calcium altroheptonate, calcium glucoheptonate, calcium mannoheptonate, calcium guloheptonate, calcium idoheptonate, calcium galactoheptonate, calcium taloheptonate, calcium tartronate, calcium malate, calcium tartrate, calcium citrate, calcium saccharate, calcium mucate, calcium lactate, calcium lactogluconate, calcium ascorbate, calcium isocitrate, and calcium citramalate, and mixtures thereof. It was surprisingly found that the composition was particularly effective inhibitor of post harvest diseases in fruits and vegetables. It has surprisingly and unexpectedly been found that use of at least one salt as defined above with at least one antagonistic micro-organism according to the present invention facilitates improved control of plant pathogens. The combination of the salts as described herein and the antagonistic microorganism offers effective control of a major postharvest rot of fruit and gives better control over use of an antagonist alone at the same concentration or gives similar control over use of high amount of $CaCl_2$ (2%) with the microorganism. The composition has particularly antifungal and antibacterial activity.

According to an embodiment of the present invention, said at least one antagonistic micro-organism is selected from the group comprising bacteria, fungus and yeast. In a particular embodiment, said antagonistic microorganism is selected from the group comprising *Agrobacterium* spp., *Ampelomyces* spp., *Aureobasidium* spp; *Bacillus* spp., *Bulleromyces* spp., *Candida* spp., *Chaetomium* spp., *Coniothyrium* spp., *Cryptococcus* spp., *Debaryomyces* spp., *Dekkera* spp., *Erwinia* spp., *Exophilia* spp., *Gliocladium* spp., *Hansenula* spp. *Issatchenkia* spp., *Kluyveromyces* spp., *Mariannaea* spp., *Metschnikovia* spp., *Microdochium* spp., *Penicillium* spp., *Phlebiopsis* spp.; *Pichia* spp., *Pseudomonas* spp., *Pseudozyma* spp., *Rhodotorula* spp., *Saccharomyces* spp., *Sporobolomyces* spp., *Streptomyces* sp., *Talaromyces* spp., *Trichoderma* spp., *Ulocladium* spp., *Zygosaccharomyces* spp.

In a particular embodiment, said antagonistic microorganism is selected from preferably *Agrobacterium radiobacter, Bacillus subtilis, Bacillus licheniformis, Bacillus pumilis, Candida oleophila, Candida saitoana, Candida sake, Candida tenius, Candida utilis, Coniothyrium minitans, Cryptococcus albidus, Erwinia carotovora, Gliocladium catenalatum, Gliocladium virens, Hanseniaspora uvarum, Kluyveromyces thermotolerance, Metschnikovia fructicola, Metschnikowia reukafii, Microdochium dimerum, Penicillium oxalicum, Phlebiopsis gigantean, Pichia anomala, Pichia guilliermondii, Pseudomonas cepacia, Pseudomonas chlororaphis, Pseudomonas fluorescens, Pseudomonas syringae, Pseudozyma flocullosa, Rhodotorula glutinis, Rhodotorula mucilaginosa, Saccharomyces cerevisiae, Streptomyces griseoviridis, Talaromyces flavus, Trichoderma atroviride, Trichoderma harzianum, Trichoderma polysporum, Trichoderma viride*, or *Ulocladium atrum*.

In an embodiment of the invention, the yeast is *Candida oleophila* or *Pichia anomala*. The *Candida oleophila* strain can be under the form of a strain consisting of *Candida oleophila* Montrocher strain O deposited under MUCL-40564, deposited on Jun. 17, 1997 at the BBCM™/MUCL Culture Collection of the Mycothèque de l'Université Catholique de Louvain, and *Candida oleophila* Montrocher commercial strain I-182.

In an embodiment, the composition according to the invention comprises a combination of one salt with one antagonistic microorganism, said combination being selected from $CaHPO_4$+*Pseudomonas syringae*, $Ca_3(PO_4)_3$+*Pseudomonas syringae*, $Ca(CO_3)$+*Pseudomonas syringae*, $Ca(HCO_3)_2$+*Pseudomonas syringae*, calcium acetate+*Pseudomonas syringae*, calcium glutamate+*Pseudomonas syringae*, $CaHPO_4$+*Bacillus subtilis*, $Ca_3(PO_4)_3$+*Bacillus subtilis*, $Ca(CO_3)$+*Bacillus subtilis*, $Ca(HCO_3)_2$+*Bacillus subtilis*, calcium acetate+*Bacillus subtilis*, calcium glutamate+*Bacillus subtilis*, $CaHPO_4$+*Bacillus pumilis*, $Ca_3(PO_4)_3$+*Bacillus pumilis*, $Ca(CO_3)$+*Bacillus pumilis*, $Ca(HCO_3)_2$+*Bacillus pumilis*, calcium acetate+*Bacillus pumilis*, calcium glutamate+*Bacillus pumilis*, $CaHPO_4$+*Candida oleophila*, $Ca_3(PO_4)_3$+*Candida oleophila*, $Ca(CO_3)$+*Candida oleophila*, $Ca(HCO_3)_2$+*Candida oleophila*, calcium acetate+*Candida oleophila*, calcium glutamate+*Candida oleophila*, $CaHPO_4$+*Candida saitoana*, $Ca_3(PO_4)_3$+*Candida saitoana*, $Ca(CO_3)$+*Candida saitoana*, $Ca(HCO_3)_2$+*Candida saitoana*, calcium acetate+*Candida saitoana*, calcium glutamate+*Candida saitoana*, $CaHPO_4$+*Candida sake*, $Ca_3(PO_4)_3$+*Candida sake*, $Ca(CO_3)$+*Candida sake*, $Ca(HCO_3)_2$+*Candida sake*, calcium acetate+*Candida sake*, calcium glutamate+*Candida sake*, $CaHPO_4$+*Kluyveromyces* sp., $Ca_3(PO_4)_3$+*Kluyveromyces* sp., $Ca(CO_3)$+*Kluyveromyces* sp., $Ca(HCO_3)_2$+*Kluyveromyces* sp., calcium acetate+*Kluyveromyces* sp., calcium glutamate+*Kluyveromyces* sp., $CaHPO_4$+*Metschnikovia fructicola*, $Ca_3(PO_4)_3$+*Metschnikovia fructicola*, $Ca(CO_3)$+*Metschnikovia fructicola*, $Ca(HCO_3)_2$+*Metschnikovia fructicola*, calcium acetate+*Metschnikovia fructicola*, calcium glutamate+*Metschnikovia fructicola*, $CaHPO_4$+*Microdochium* sp., $Ca_3(PO_4)_3$+*Microdochium* sp., $Ca(CO_3)$+*Microdochium* sp., $Ca(HCO_3)_2$+*Microdochium* sp., calcium acetate+*Microdochium* sp., calcium glutamate+*Microdochium* sp., $CaHPO_4$+*Pichia anomala*, $Ca_3(PO_4)_3$+*Pichia anomala*, $Ca(CO_3)$+*Pichia anomala*, $Ca(HCO_3)_2$+*Pichia anomala*, calcium acetate+*Pichia anomala*, calcium glutamate+*Pichia anomala*, CaHPO$_4$+*Pichia guilliermondii*, Ca$_3$(PO$_4$)$_3$+*Pichia guilliermondii*, Ca(CO$_3$)+*Pichia guilliermondii*, Ca(HCO$_3$)$_2$+*Pichia guilliermondii*, calcium acetate+*Pichia* calcium glutamate+*Pichia guilliermondii*, CaHPO$_4$+*Trichoderma* atroviride, Ca$_3$(PO$_4$)$_3$+*Trichoderma atroviride*, Ca(CO$_3$)+*Trichoderma atroviride*, Ca(HCO$_3$)$_2$+*Trichoderma* atroviride, calcium acetate+*Trichoderma atroviride*, calcium glutamate+*Trichoderma* atroviride, CaHPO$_4$+*Trichoderma harzianum*, Ca$_3$(PO$_4$)$_3$+*Trichoderma harzianum*, Ca(CO$_3$)+*Trichoderma harzianum*, Ca(HCO$_3$)$_2$+*Trichoderma harzianum*, calcium acetate+*Trichoderma harzianum*, calcium glutamate+*Trichoderma harzianum*, CaHPO$_4$+*Trichoderma polysporum*, Ca$_3$(PO$_4$)$_3$+*Trichoderma* polysporum, Ca(CO$_3$)+*Trichoderma polysporum*, Ca(HCO$_3$)$_2$+*Trichoderma polysporum*, calcium acetate+*Trichoderma polysporum*, calcium glutamate+*Trichoderma polysporum*, CaHPO$_4$+*Trichoderma viride*, Ca$_3$(PO$_4$)$_3$+*Trichoderma viride*, Ca(CO$_3$)+*Trichoderma viride*, Ca(HCO$_3$)$_2$+*Trichoderma viride*, calcium acetate+*Trichoderma viride* or calcium glutamate+*Trichoderma viride*.

In another embodiment, said combination is selected from calcium gluconate+*Pseudomonas syringae*, calcium gluconate+*Bacillus subtilis*, calcium gluconate+*Bacillus* pumilis, calcium gluconate+*Candida oleophila*, calcium gluconate+*Candida saitoana*, calcium gluconate+*Candida sake*, calcium gluconate+*Kluyveromyces* sp., calcium gluconate+*Metschnikovia fructicola*, calcium gluconate+*Microdochium* sp., calcium gluconate+*Pichia anomala*, calcium gluconate+*Pichia guilliermondii*, calcium tartrate+*Pseudomonas syringae*, calcium citrate+*Pseudomonas syringae*, calcium lactogluconate+*Pseudomonas syringae*, calcium ascorbate+*Pseudomonas syringae*, calcium isocitrate+*Pseudomonas syringae*, calcium citramalate+*Pseudomonas syringae*, calcium tartrate+*Bacillus subtilis*, calcium citrate+*Bacillus subtilis*, calcium lactogluconate+*Bacillus subtilis*, calcium ascorbate+*Bacillus subtilis*, calcium isocitrate+*Bacillus subtilis*, calcium citramalate+*Bacillus subtilis*, calcium tartrate+*Bacillus pumilis*, calcium citrate+*Bacillus* pumilis, calcium lactogluconate+*Bacillus pumilis*, calcium ascorbate+*Bacillus pumilis*, calcium isocitrate+*Bacillus pumilis*, calcium citramalate+*Bacillus pumilis*, calcium tartrate+*Candida oleophila*, calcium citrate+*Candida oleophila*, calcium gluconate+*Trichoderma* atroviride, calcium gluconate+*Trichoderma harzianum*, calcium gluconate+*Trichoderma* polysporum, calcium gluconate+*Trichoderma viride*, or calcium tartrate+*Trichoderma* atroviride.

In another embodiment, said combination is selected from calcium lactogluconate+*Candida oleophila*, calcium ascorbate+*Candida oleophila*, calcium isocitrate+*Candida* oleophila, calcium citramalate+*Candida oleophila*, calcium tartrate+*Candida saitoana*, calcium citrate+*Candida saitoana*, calcium lactogluconate+*Candida saitoana*, calcium ascorbate+*Candida saitoana*, calcium isocitrate+*Candida saitoana*, calcium citramalate+*Candida saitoana*, calcium tartrate+*Candida sake*, calcium citrate+*Candida sake*, calcium lactogluconate+*Candida sake*, calcium ascorbate+*Candida sake*, calcium isocitrate+*Candida sake*, calcium citramalate+*Candida sake*, calcium tartrate+*Kluyveromyces* sp., calcium citrate+*Kluyveromyces* sp., calcium lactogluconate+*Kluyveromyces* sp., calcium ascorbate+*Kluyveromyces* sp., calcium isocitrate+*Kluyveromyces* sp., calcium citramalate+*Kluyveromyces* sp., calcium tartrate+*Metschnikovia fructicola*, calcium citrate+*Metschnikovia fructicola*, calcium lactogluconate+*Metschnikovia fructicola*, calcium ascorbate+*Metschnikovia fructicola*, calcium isocitrate+*Metschnikovia fructicola*, calcium citramalate+*Metschnikovia fructicola*, calcium tartrate+*Microdochium* sp., calcium citrate+*Microdochium* sp., calcium lactogluconate+*Microdochium* sp., calcium ascorbate+*Microdochium* sp., calcium isocitrate+*Microdochium* sp., calcium citramalate+*Microdochium* sp., calcium tartrate+*Pichia anomala*, calcium citrate+*Pichia anomala*, calcium lactogluconate+*Pichia anomala*, calcium ascorbate+*Pichia anomala*, calcium isocitrate+*Pichia anomala*, calcium citramalate+*Pichia anomala*, calcium tartrate+*Pichia guilliermondii*, calcium citrate+*Pichia guilliermondii*, calcium lactogluconate+*Pichia* guilliermondii, calcium ascorbate+*Pichia guilliermondii*, calcium isocitrate+*Pichia* guilliermondii, calcium citramalate+*Pichia guilliermondii*, calcium lactogluconate+*Trichoderma atroviride*, calcium ascorbate+*Trichoderma atroviride*, calcium isocitrate+*Trichoderma atroviride*, calcium citramalate+*Trichoderma atroviride*, calcium tartrate+*Trichoderma harzianum*, calcium citrate+*Trichoderma harzianum*, calcium lactogluconate+*Trichoderma harzianum*, calcium ascorbate+*Trichoderma harzianum*, calcium isocitrate+*Trichoderma harzianum*, calcium citramalate+*Trichoderma harzianum*, calcium tartrate+*Trichoderma polysporum*, calcium citrate+*Trichoderma polysporum*, calcium lactogluconate+*Trichoderma polysporum*, calcium ascorbate+*Trichoderma polysporum*, calcium isocitrate+*Trichoderma polysporum*, calcium citramalate+*Trichoderma* polysporum, calcium tartrate+*Trichoderma viride*, calcium citrate+*Trichoderma viride*, calcium lactogluconate+*Trichoderma viride*, calcium ascorbate+*Trichoderma viride*, calcium isocitrate+*Trichoderma viride*, or calcium citramalate+*Trichoderma viride.*

The present invention also encompasses compositions comprising at least one antagonistic microorganism and at least two salts as described herein above. The present invention also encompasses compositions comprising at least two antagonistic microorganisms and at least one salt as described herein above.

As used in the specification and the appended claims, the singular forms "a", "an," and "the" include plural referents unless the context clearly dictates otherwise. By way of example, "a compound" means one compound or more than one compound.

The recitation of numerical ranges by endpoints includes all integer numbers and, where appropriate, fractions subsumed within that range (e.g. 1 to 5 can include 1, 1.1, 1.15, 1.2, 1.3, 1.4, 1.5, 2, 2.75, 3, 3.80, 4, and 5).

As used herein, the term "derivatives" is means chemical derivatives, such as for instance solvates, hydrates stereoisomeric forms, racemic mixtures, and esters. As used herein and unless otherwise stated, the term "solvate" includes any combination which may be formed by the salt with a suitable inorganic solvent (e.g. hydrates) or organic solvent, such as but not limited to alcohols, ketones, esters and the like.

All stereoisomers of the salts as described herein are included within the scope of the invention, as pure compounds as well as mixtures thereof. Individual enantiomers, diastereomers, geometric isomers, and combinations and mixtures thereof are all encompassed by the present invention. Pure stereoisomeric forms of the salts and intermediates as mentioned herein are defined as isomers substantially free of other enantiomeric or diastereomeric forms of the same basic molecular structure of said compounds or intermediates.

As used herein, the term "enhancing compound", means, a compound which is capable of enhancing the biological properties of a micro-organism. For example, it may boost the biological properties of antagonistic micro-organisms against pathogens able to cause diseases to vegetal material.

As used herein, the term "antagonistic micro-organism" means a micro-organism which is an antagonist to a pathogen such as for example a pathogen which is capable to cause diseases to plants or animal including humans. In a preferred embodiment said micro-organism is an antagonist to a pathogen such as for example a pathogen which is liable to cause diseases to vegetal material. Such antagonistic microorganism can be selected from the group comprising bacteria, fungus and yeast.

As used herein, the term "biopesticide" encompasses biofungicide, biobactericide and biovirucide.

The compositions of the present invention may further comprise in addition to the salt and the micro-organism, at least one mannans and/or derivatives thereof. The amount of said mannans may be in the range of 0.001% and 2% w/v, preferably in the range of 0.001 and 0.2% w/v.

The present invention therefore provides a composition which can be used as phytopharmaceutical and pharmaceutical composition in the treatment of plants and animals against microbial infections including bacterial, yeast, fungal, viral and protozoan infections.

In particular, the present compositions showed an improved efficacy against diseases caused by pathogens to vegetal material, for instance diseases caused by moulds that colonize parts of plants, either after harvesting or during the plant life cycle. Exemplary species of plant pathogens which can be inhibited by the present composition include, but are not limited to, *Alternaria* spp., *Ascochyta* spp., *Aspergillus* spp., *Botrytis* spp., *Cercospora* spp., *Cladosporium* spp., *Claviceps* spp., *Colletotrichum* spp., *Erysiphe* spp., *Fusarium* spp., *Geotrichum* spp., *Gilbertella* spp., *Gloeosporium* spp., *Helminthosporium* spp., *Monilia* spp., *Monilinia* spp., *Mucov* spp., *Nectria* spp., *Penicillium* spp., *Peronospora* spp., *Pezicula* spp., *Phomopsis* spp., *Phytophthora* spp., *Plasmopara* spp., *Podosphaera* spp., *Pseudocercosporium* spp., *Puccinia* spp., *Rhizoctonia* spp., *Rhizopus* spp., *Rynchosporium* spp., *Sclerotinia* spp., *Septoria* spp., *Sphaerotheca* spp., *Uncinula* spp., *Ustilago* spp., *Venturia* spp., *Verticillium* spp., and bacterial or viral pathogens. In a particular embodiment the plant pathogens may be selected from the group comprising *Alternaria alternata*, *Ascochyta* sp., *Aspergillus flavus*, *Aspergillus niger*, *Botrytis alii*, *Botrytis cinerea*, *Botrytis fabae*, *Cercospora* sp., *Cladosporium* sp., *Claviceps purpurea*, *Colletotrichum* sp., *Erysiphe betae*, *Erysiphe graminis*, *Fusarium oxysporum*, *Geotrichum candidum*, *Gilbertella persicovia*, *Gloeosporium perennans*, *Gloeosporium fructigenum*, *Helminthosporium* sp., *Monilia* sp., *Monilinia fructicola*, *Monilinia laxa*, *Mucov* sp., *Nectria cinnabarina*, *Penicillium digitatum*, *Penicillium expansum*, *Penicillium italicum*, *Peronospora* sp., *Pezicula malicorticas*, *Phomopsis viticola*, *Phytophthora infestans*, *Plasmopara viticola*, *Podosphaera leucotricha*, *Pseudocercosporium* sp., *Puccinia graminis*, *Rhizoctonia* sp., *Rhizopus arrhizus*, *Rhizopus stolonifer*, *Rynchosporium* sp., *Sclerotinia Cepivorum*, *Sclerotinia sclerotiorum*, *Septoria apicola*, *Sphaerotheca* sp., *Uncinula necator*, *Ustilago* sp., *Venturia inaequalis*; *Verticillium albo-atrum*, and *Verticillium dahliae*. In a particular embodiment the plant pathogens may be selected from the group comprising *Botrytis* spp., *Penicillium* spp., *Pezicula* spp., and *Rhizopus* spp. For example the pathogens may be *Botrytis cinerea*, *Penicillium digitatum*, *Penicillium expansum*, *Penicillium italicum*, *Pezicula* spp., and *Rhizopus* spp.

In a preferred embodiment, the composition of the present invention is particularly useful as a biopesticide.

According to the present invention, the antagonistic micro-organism and the salt as described herein and/or derivatives thereof can be provided as a mixture of the micro-organism and salt as described herein. According to another embodiment of the present invention, the antagonistic micro-organism and the salt as described herein can be provided as separate, unmixed preparations, which are to be mixed for making the present composition. For example, the antagonistic micro-organism and salt as described herein may be present in a kit, individually packed, or packed together in a ready mixed form. The antagonistic micro-organism and salt as described herein can be present in the kit as separate, unmixed preparations or together in one preparation.

The present invention further encompasses a method for the manufacture of a composition according to the present invention comprising the step of mixing at least one antagonistic micro-organism with at least one salt as described herein.

A further aspect of the invention is a composition comprising at least one antagonistic micro-organism and at least one salt as described herein and/or derivatives thereof, for simultaneous, separate or sequential administration to a subject to be treated.

As used herein the term "subject" encompasses, plants or animals including humans to be treated. In an embodiment of the present invention the subject is plants such as vegetable material.

Yet a further aspect of the invention is a method for treating plant material comprising administering thereto an effective amount of at least one antagonistic micro-organism of the invention and at least one salt as described herein and/or derivatives thereof, simultaneously, separately or sequentially.

By simultaneous administration means the antagonistic micro-organism and the salt as described herein are administered to the plant at the same time. For example, as a mixture of the antagonistic micro-organism and salt as described herein, or a composition comprising said antagonistic micro-organism and salt as described herein.

By separate administration means the antagonistic micro-organism and the salt are administered to a plant material at the same time or substantially the same time. The antagonistic micro-organism and salt are administered as separate, unmixed preparations. For example, the antagonistic micro-organism and salt may be present in the kit as individually packed.

The enhanced ability of the antagonistic micro-organism to control plant pathogens in the presence of at least one salt as described herein above is especially unexpected. The present invention provides a biopesticide composition which comprises lower concentrations of antagonistic micro-organisms while prolonging the duration of the efficiency of the compositions against the pathogens.

Furthermore, the invention also relates to the use of a salt as described herein as a compound for enhancing the efficacy of composition comprising at least one antagonistic micro-organism, as compared to the efficacy of that microorganism alone. Salts such as calcium gluconate, calcium acetate, calcium citrate, calcium carbonate, calcium bicarbonate, calcium phosphate, calcium lactate, calcium lactogluconate, calcium ascorbate, were shown to particularly boost the biological anti-pathogen efficacy of a composition comprising at least one micro-organism.

The invention also relates to the use of at least one salt as described herein as an enhancing compound for lowering the concentration of an antagonistic micro-organism without lowering the efficiency of the composition against pathogens. The present invention further relates to the use of at least one salt as described herein as an enhancing compound for lowering the concentration of an antagonistic micro-organism while prolonging the duration of the efficiency of the composition against pathogens.

In said method, boosting the biological properties of the micro-organism or a micro-organism based composition may comprise lowering the concentration of an antagonistic micro-organism without lowering the efficiency of the composition against pathogens. Enhancing and amplifying the biological properties may also comprise lowering the concentration of an antagonistic micro-organism while prolonging the duration of the efficiency of the composition against pathogens. Because of the surprising increased effect of the present composition, the present invention permits to use lower concentration of the composition.

The present invention also relates to a method for treating plant material such as fruits and vegetables for the control of post harvest diseases by the application of effective amounts of the novel composition.

The invention also relates to a method for boosting the properties of a biofungicide, biobactericide and/or bioviru-cide in a composition comprising adding at least salt as described herein as an enhancing compound to said composition. More in particular, the present invention encompasses the use of at least one salt as described herein and/or derivative thereof as a compound for enhancing the properties of biofungicide, biobactericide and/or biovirucide.

The present invention also provides a composition for use against one or more pathogens comprising a composition according to the invention and at least one agrochemical compound. In an embodiment of the present invention, the agrochemical compound can be selected from the group comprising fungicide, bactericide, nematicide, insecticide, herbicide and the like.

The invention also relates to a method for boosting the properties of at least one agrochemical in a composition comprising adding at least a salt as described herein as an enhancing compound to said composition. More in particular, the present invention encompasses the use of at least one salt as described herein and/or derivative thereof as a compound for enhancing the properties of at least one agrochemical compound. For example, the pesticide properties of a chemical compound can be boosted by the addition of at least one salt as described herein. The present invention therefore also provides a composition for use against one or more pathogens comprising at least one salt as described herein and/or derivative thereof and one agrochemical compound. In an embodiment of the present invention the agrochemical compound can be selected from the group comprising fungicide, bactericide, nematicide, insecticide, herbicide and the like.

The invention will be further illustrated below by the description of some ways of carrying it out.

Example 1

Salts and antagonistic microorganism encompassed in the composition of the present invention are listed in Tables 1 and 2.

TABLE 1

| | Salts |
|---|---|
| 1 | calcium sulphate |
| 2 | Ca(H$_2$PO$_4$)$_2$ |
| 3 | CaHPO$_4$ |
| 4 | Ca$_3$(PO4)$_2$ |
| 5 | CaCO$_3$ |
| 6 | Ca(HCO$_3$)$_2$ |
| 7 | calcium acetate |
| 8 | calcium ethanoate |
| 9 | calcium glutamate |

TABLE 1-continued

| | Salts |
|---|---|
| 10 | calcium glycerate |
| 11 | calcium erythronate |
| 12 | calcium theonate |
| 13 | calcium ribonate |
| 14 | calcium arabinoate |
| 15 | calcium xylonate |
| 16 | calcium lyxonate |
| 17 | calcium allonate |
| 18 | calcium altronate |
| 19 | calcium gluconate |
| 20 | calcium mannoate |
| 21 | calcium gulonate |
| 22 | calcium idonate |
| 23 | calcium galactonate |
| 24 | calcium talonate |
| 25 | calcium alloheptonate |
| 26 | calcium altroheptonate |
| 27 | calcium glucoheptonate |
| 28 | calcium mannoheptonate |
| 29 | calcium guloheptonate |
| 30 | calcium idoheptonate |
| 31 | calcium galactoheptonate |
| 32 | calcium taloheptonate |
| 33 | calcium tartronate |
| 34 | calcium malate |
| 35 | calcium tartrate |
| 36 | calcium citrate |
| 37 | calcium saccharate |
| 38 | calcium mucate |
| 39 | calcium lactogluconate |
| 40 | calcium ascorbate |
| 41 | calcium isocitrate |
| 42 | calcium citramalate |

TABLE 2

| | Antagonistic microorganism |
|---|---|
| a | *Agrobacterium radiobacter* |
| b | *Bacillus subtilis* |
| c | *Bacillus licheniformis* |
| d | *Bacillus pumilis* |
| e | *Candida oleophila* |
| f | *Candida saitoana* |
| g | *Candida sake* |
| h | *Candida tenius* |
| i | *Candida utilis* |
| j | *Coniothyrium minitans* |
| k | *Erwinia carotovora* |
| l | *Gliocladium catenalatum* |
| m | *Gliocladium virens* |
| n | *Hanseniaspora uvarum* |
| o | *Kluyveromyces* sp. |
| p | *Metschnikovia fructicola* |
| q | *Microdochium* sp. |
| r | *Penicillium oxalicum* |
| s | *Phlebiopsis gigantean* |
| t | *Pichia anomala* |
| u | *Pichia guilliermondii* |
| v | *Pseudomonas cepacia* |
| w | *Pseudomonas chlororaphis* |
| x | *Pseudomonas fluorescens* |
| y | *Pseudomonas syringae* |
| z | *Pseudozyma flocullosa* |
| aa | *Rhodotorula glutinis* |
| bb | *Rhodotorula mucilaginosa* |
| cc | *Streptomyces griseoviridis* |
| dd | *Talaromyces flavus* |
| ee | *Trichoderma atroviride* |
| ff | *Trichoderma harzianum* |
| gg | *Trichoderma polysporum* |
| hh | *Trichoderma viride* |
| ii | *Ulocladium atrum* |

The present invention encompasses any combination of one or more salts 1 to 43 with one or more antagonistic microorganism a to ii. In an embodiment, the composition according to the invention comprises a combination of one salt with one antagonistic microorganism, said combination being selected from the group comprising 1+a, 2+a, 3+a, 4+a, 5+a, 6+a, 7+a, 8+a, 9+a, 10+a, 1+b, 2+b, 3+b, 4+b, 5+b, 6+b, 7+b, 8+b, 9+b, 10+b, 1+c, 2+c, 3+c, 4+c, 5+c, 6+c, 7+c, 8+c, 9+c, 10+c, 1+d, 2+d, 3+d, 4+d, 5+d, 6+d, 7+d, 8+d, 9+d, 10+d, 1+e, 2+e, 3+e, 4+e, 5+e, 6+e, 7+e, 8+e, 9+e, 10+e, 1+f, 2+f, 3+f, 4+f, 5+f, 6+f, 7+f, 8+f, 9+f, 10+f, 1+g, 2+g, 3+g, 4+g, 5+g, 6+g, 7+g, 8+g, 9+g, 10+g, 1+h, 2+h, 3+h, 4+h, 5+h, 6+h, 7+h, 8+h, 9+h, 10+h, 1+i, 2+i, 3+i, 4+i, 5+i, 6+i, 7+i, 8+i, 9+i, 10+i, 1+j, 2+j, 3+j, 4+j, 5+j, 6+j, 7+j, 8+j, 9+j, 10+j, 1+k, 2+k, 3+k, 4+k, 5+k, 6+k, 7+k, 8+k, 9+k, 10+k, 1+l, 2+l, 3+l, 4+l, 5+l, 6+l, 7+l, 8+l, 9+l, 10+l, 1+m, 2+m, 3+m, 4+m, 5+m, 6+m, 7+m, 8+m, 9+m, 10+m, 1+n, 2+n, 3+n, 4+n, 5+n, 6+n, 7+n, 8+n, 9+n, 10+n, 1+o, 2+o, 3+o, 4+o, 5+o, 6+o, 7+o, 8+o, 9+o, 10+o, 1+p, 2+p, 3+p, 4+p, 5+p, 6+p, 7+p, 8+p, 9+p, 10+p, 1+q, 2+q, 3+q, 4+q, 5+q, 6+q, 7+q, 8+q, 9+q, 10+q, 1+r, 2+r, 3+r, 4+r, 5+r, 6+r, 7+r, 8+r, 9+r, 10+r, 1+s, 2+s, 3+s, 4+s, 5+s, 6+s, 7+s, 8+s, 9+s, 10+s, 1+t, 2+t, 3+t, 4+t, 5+t, 6+t, 7+t, 8+t, 9+t, 10+t, 1+u, 2+u, 3+u, 4+u, 5+u, 6+u, 7+u, 8+u, 9+u, 10+u, 1+v, 2+v, 3+v, 4+v, 5+v, 6+v, 7+v, 8+v, 9+v, 10+v, 1+w, 2+w, 3+w, 4+w, 5+w, 6+w, 7+w, 8+w, 9+w, 10+w, 1+x, 2+x, 3+x, 4+x, 5+x, 6+x, 7+x, 8+x, 9+x, 10+x, 11+a, 12+a, 13+a, 14+a, 15+a, 16+a, 17+a, 18+a, 11+b, 12+b, 13+b, 14+b, 15+b, 16+b, 17+b, 18+b, 11+c, 12+c, 13+c, 14+c, 15+c, 16+c, 17+c, 18+c, 11+d, 12+d, 13+d, 14+d, 15+d, 16+d, 17+d, 18+d, 11+e, 12+e, 13+e, 14+e, 15+e, 16+e, 17+e, 18+e, 11+f, 12+f, 13+f, 14+f, 15+f, 16+f, 17+f, 18+f, 11+g, 12+g, 13+g, 14+g, 15+g, 16+g, 17+g, 18+g, 11+h, 12+h, 13+h, 14+h, 15+h, 16+h, 17+h, 18+h, 11+i, 12+i, 13+i, 14+i, 15+i, 16+i, 17+i, 18+i, 11+j, 12+j, 13+j, 14+j, 15+j, 16+j, 17+j, 18+j, 11+k, 12+k, 13+k, 14+k, 15+k, 16+k, 17+k, 18+k, 11+l, 12+l, 13+l, 14+l, 15+l, 16+l, 17+l, 18+l, 11+m, 12+m, 13+m, 14+m, 15+m, 16+m, 17+m, 18+m, 11+n, 12+n, 13+n, 14+n, 15+n, 16+n, 17+n, 18+n, 11+o, 12+o, 13+o, 14+o, 15+o, 16+o, 17+o, 18+o, 1+aa, 2+aa, 3+aa, 4+aa, 5+aa, 6+aa, 7+aa, 8+aa, 9+aa, 10+aa, 1+bb, 2+bb, 3+bb, 4+bb, 5+bb, 6+bb, 7+bb, 8+bb, 9+bb, 10+bb, 1+cc, 2+cc, 3+cc, 4+cc, 5+cc, 6+cc, 8+cc, 9+cc, 10+cc, 1+dd, 2+dd, 3+dd, 4+dd, 5+dd, 6+dd, 7+dd, 8+dd, 9+dd, 10+dd, 1+ee, 2+ee, 3+ee, 4+ee, 5+ee, 6+ee, 7+ee, 8+ee, 9+ee, 10+ee, 1+ff, 2+ff, 3+ff, 4+ff, 5+ff, 6+ff, 7+ff, 8+ff, 9+ff, 10+ff, 1+gg, 2+gg, 3+gg, 4+gg, 5+gg, 6+gg, 7+gg, 8+gg, 9+gg, 10+gg, 1+hh, 3+hh, 4+hh, 5+hh, 6+hh, 7+hh, 8+hh, 9+hh, 10+hh, 1+ii, 2+ii, 3+ii, 4+ii, 5+ii, 6+ii, 7+ii, 8+ii, 9+ii, 10+ii, 11+aa, 12+aa, 13+aa, 14+aa, 15+aa, 16+aa, 17+aa, 18+aa, 11+bb, 12+bb, 13+bb, 14+bb, 15+bb, 16+bb, 17+bb, 18+bb, 11+cc, 12+cc, 13+cc, 14+cc, 15+cc, 16+cc, 17+cc, 18+cc, 11+dd, 12+dd, 13+dd, 14+dd, 15+dd, 16+dd, 17+dd, 18+dd, 11+ee, 12+ee, 13+ee, 14+ee, 15+ee, 16+ee, 17+ee, 18+ee, 11+ff, 12+ff, 13+ff, 14+ff, 15+ff, 16+ff, 17+ff, 18+ff, 11+gg, 12+gg, 13+gg, 14+gg, 15+gg, 16+gg, 17+gg, 18+gg, 11+hh, 12+hh, 13+hh, 14+hh, 15+hh, 16+hh, 17+hh, 18+hh, 11+ii, 12+ii, 13+ii, 14+ii, 15+ii, 17+ii, 18+ii and 11+p.

In another embodiment, the composition according to the invention comprises a combination of one salt with one antagonistic microorganism, said combination being selected from the group comprising 12+p, 13+p, 14+p, 15+p, 16+p, 17+p, 18+p, 11+q, 12+q, 13+q, 14+q, 15+q, 16+q, 17+q, 18+q, 11+r, 12+r, 13+r, 14+r, 15+r, 16+r, 17+r, 18+r, 11+s, 12+s, 13+s, 14+s, 15+s, 16+s, 17+s, 18+s, 11+t, 12+t, 13+t, 14+t, 15+t, 16+t, 17+t, 18+t, 11+u, 12+u, 13+u, 14+u, 15+u, 16+u, 17+u, 18+u, 11+v, 12+v, 13+v, 14+v, 15+v, 16+v, 17+v, 18+v, 11+w, 12+w, 13+w, 14+w, 15+w, 16+w, 17+w, 18+w, 11+x, 12+x, 13+x, 14+x, 15+x, 16+x, 17+x, 18+x, 19+a, 20+a, 21+a, 22+a, 23+a, 24+a, 25+a, 26+a, 27+a, 28+a, 29+a, 30+a, 19+b, 20+b, 21+b, 22+b, 23+b, 24+b, 25+b, 26+b, 27+b, 28+b, 29+b, 30+b, 19+c, 20+c, 21+c, 22+c, 23+c, 24+c, 25+c, 26+c, 27+c, 28+c, 29+c, 30+c, 19+d, 20+d, 21+d, 22+d, 23+d, 24+d, 25+d, 26+d, 27+d, 28+d, 29+d, 30+d, 19+e, 20+e, 21+e, 22+e, 23+e, 24+e, 25+e, 26+e, 27+e, 28+e, 29+e, 30+e, 19+f, 20+f, 21+f, 22+f, 23+f, 24+f, 25+f, 26+f, 27+f, 28+f, 29+f, 30+f, 19+g, 20+g, 21+g, 22+g, 23+g, 24+g, 25+g, 26+g, 27+g, 28+g, 29+g, 30+g, 19+h, 20+h, 21+h, 22+h, 23+h, 24+h, 25+h, 26+h, 27+h, 28+h, 29+h, 30+h, 19+i, 20+i, 21+i, 22+i, 23+i, 24+i, 25+i, 26+i, 27+i, 28+i, 29+i, 30+i, 19+j, 20+j, 21+j, 22+j, 23+j, 24+j, 25+j, 26+j, 27+j, 28+j, 29+j, 30+j, 19+k, 20+k, 21+k, 22+k, 23+k, 24+k, 25+k, 26+k, 27+k, 28+k, 29+k, 30+k, 19+l, 20+l, 21+l, 22+l, 23+l, 24+l, 25+l, 26+l, 27+l, 28+l, 29+l, 30+l, 19+m, 20+m, 21+m, 22+m, 23+m, 24+m, 25+m, 26+m, 27+m, 28+m, 29+m, 30+m, 19+n, 20+n, 21+n, 22+n, 23+n, 24+n, 25+n, 26+n, 27+n, 28+n, 29+n, 30+n, 19+o, 20+o, 21+o, 22+o, 23+o, 24+o, 25+o, 26+o, 27+o, 28+o, 29+o, 30+o, 19+p, 20+p, 21+p, 22+p, 23+p, 24+p, 25+p, 26+p, 27+p, 28+p, 29+p, 30+p, 19+q, 20+q, 21+q, 22+q, 23+q, 24+q, 25+q, 26+q, 27+q, 28+q, 29+q, 30+q, 19+r, 20+r, 21+r, 22+r, 23+r, 24+r, 25+r, 26+r, 27+r, 28+r, 29+r, 30+r, 19+s, 20+s, 21+s, 22+s, 23+s, 24+s, 25+s, 26+s, 27+s, 28+s, 29+s, 30+s, 19+t, 20+t, 21+t, 22+t, 23+t, 24+t, 25+t, 26+t, 27+t, 28+t, 29+t, 30+t, 19+u, 20+u, 21+u, 22+u, 23+u, 24+u, 25+u, 26+u, 27+u, 28+u, 29+u, 30+u, 19+v, 20+v, 21+v, 22+v, 23+v, 24+v, 25+v, 26+v, 27+v, 28+v, 29+v, 30+v, 19+w, 20+w, 21+w, 22+w, 23+w, 24+w, 25+w, 26+w, 27+w, 28+w, 29+w, 30+w, 19+x, 20+x, 21+x, 22+x, 23+x, 24+x, 25+x, 26+x, 27+x, 28+x, 29+x, 30+x, 31+a, 32+a, 33+a, 34+a, 35+a, 36+a, 37+a, 38+a, 39+a, 40+a, 41+a, 42+a, 31+b, 32+b, 33+b, 34+b, 35+b, 36+b, 37+b, 38+b, 39+b, 40+b, 41+b, 42+b, 31+c, 32+c, 33+c, 34+c, 35+c, 36+c, 37+c, 38+c, 39+c, 40+c, 41+c, 42+c, 31+d, 32+d, 33+d, 34+d, 35+d, 36+d, 37+d, 38+d, 39+d, 40+d, 41+d, 42+d, 31+e, 32+e, 33+e, 34+e, 35+e, 36+e, 37+e, 38+e, 19+aa, 20+aa, 21+aa, 22+aa, 23+aa, 24+aa, 25+aa, 26+aa, 27+aa, 28+aa, 29+aa, 30+aa, 19+bb, 20+bb, 21+bb, 22+bb, 23+bb, 24+bb, 25+bb, 26+bb, 27+bb, 28+bb, 29+bb, 30+bb, 19+cc, 20+cc, 21+cc, 22+cc, 23+cc, 24+cc, 25+cc, 26+cc, 27+cc, 28+cc, 29+cc, 30+cc, 19+dd, 20+dd, 21+dd, 22+dd, 23+dd, 24+dd, 25+dd, 26+dd, 27+dd, 28+dd, 29+dd, 30+dd, 19+ee, 20+ee, 21+ee, 22+ee, 23+ee, 24+ee, 25+ee, 26+ee, 27+ee, 28+ee, 29+ee, 30+ee, 19+ff, 20+ff, 21+ff, 22+ff, 23+ff, 24+ff, 25+ff, 26+ff, 27+ff, 28+ff, 29+ff, 30+ff, 19+gg, 20+gg, 21+gg, 22+gg, 23+gg, 24+gg, 25+gg, 26+gg, 27+gg, 28+gg, 29+gg, 30+gg, 19+hh, 20+hh, 21+hh, 22+hh, 23+hh, 24+hh, 25+hh, 26+hh, 27+hh, 28+hh, 29+hh, 30+hh, 19+ii, 20+ii, 21+ii, 22+ii, 23+ii, 24+ii, 25+ii, 26+ii, 27+ii, 28+ii, 29+ii, 30+ii, 31+aa, 32+aa, 33+aa, 34+aa, 35+aa, 36+aa, 37+aa, 38+aa, 39+aa, 40+aa, 41+aa, 42+aa, 31+bb, 32+bb, 33+bb, 34+bb, 35+bb, 36+bb, 37+bb, 38+bb, 39+bb, 40+bb, 41+bb, 42+bb, 31+cc, 32+cc, 33+cc, 34+cc, 35+cc, 36+cc, 37+cc, 38+cc, 39+cc, 40+cc, 41+cc, 42+cc, 31+dd, 32+dd, 33+dd, 34+dd, 35+dd, 36+dd, 37+dd, 38+dd, 39+dd, 40+dd, 41+dd, 42+dd, 31+ee, 32+ee, 33+ee, 34-Fee, 35+ee, 36+ee, 37+ee and 38+ee.

In another embodiment, the composition according to the invention comprises a combination of one salt with one antagonistic microorganism, said combination being selected from the group comprising 39+e, 40+e, 41+e, 42+e, 31+f, 32+f, 33+f, 34+f, 35+f, 36+f, 37+f, 38+f, 39+f, 40+f, 41+f, 42+f, 31+g, 32+g, 33+g, 34+g, 35+g, 36+g, 37+g, 38+g, 39+g, 40+g, 41+g, 42+g, 31+h, 32+h, 33+h, 34+h, 35+h, 36+h, 37+h, 38+h, 39+h, 40+h, 41+h, 42+h, 31+i, 32+i, 33+i, 34+i, 35+i, 36+i, 37+i, 38+i, 39+i, 40+i, 41+i, 42+i, 31+j, 32+j, 33+j, 34+j, 35+j, 36+j, 37+j, 38+j, 39+j, 40+j, 41+j, 42+j, 31+k, 32+k, 33+k, 34+k, 35+k, 36+k, 37+k, 38+k, 39+k, 40+k, 41+k, 42+k, 31+l, 32+l, 33+l, 34+l, 35+l, 36+l, 37+l, 38+l, 39+l, 40+l, 41+l, 42+l, 31+m, 32+m, 33+m, 34+m, 35+m, 36+m, 37+m, 38+m, 39+m, 40+m, 41+m, 42+m, 31+n, 32+n, 33+n, 34+n, 35+n, 36+n, 37+n, 38+n, 39+n, 40+n, 41+n, 42+n, 31+o, 32+o, 33+o, 34+o, 35+o, 36+o, 37+o, 38+o, 39+o, 40+o, 41+o, 42+o, 31+p, 32+p, 33+p, 34+p, 35+p, 36+p, 37+p, 38+p, 39+p, 40+p, 41+p, 42+p, 31+q, 32+q, 33+q, 34+q, 35+q, 36+q, 37+q, 38+q, 39+q, 40+q, 41+q, 42+q, 31+r, 32+r, 33+r, 34+r, 35+r, 36+r, 37+r, 38+r, 39+r, 40+r, 41+r, 42+r, 31+s, 32+s, 33+s, 34+s, 35+s, 36+s, 37+s, 38+s, 39+s, 40+s, 41+s, 42+s, 31+t, 32+t, 33+t, 34+t, 35+t, 36+t, 37+t, 38+t, 39+t, 40+t, 41+t, 42+t, 31+u, 32+u, 33+u, 34+u, 35+u, 36+u, 37+u, 38+u, 39+u, 40+u, 41+u, 42+u, 31+v, 32+v, 33+v, 34+v, 35+v, 36+v, 37+v, 38+v, 39+v, 40+v, 41+v, 42+v, 31+w, 32+w, 33+w, 34+w, 35+w, 36+w, 37+w, 38+w, 39+w, 40+w, 41+w, 42+w, 31+x, 32+x, 33+x, 34+x, 35+x, 36+x, 37+x, 38+x, 39+x, 40+x, 41+x, 42+x, 39+ee, 40+ee, 41+ee, 42+ee, 31+ff, 32+ff, 33+ff, 34+ff, 35+ff, 36+ff, 37+ff, 38+ff, 39+ff, 40+ff, 41+ff, 42+ff, 31+gg, 32+gg, 33+gg, 34+gg, 35+gg, 36+gg, 37+gg, 38+gg, 39+gg, 40+gg, 41+gg, 42+gg, 31+hh, 32+hh, 33+hh, 34+hh, 35+hh, 36+hh, 37+hh, 38+hh, 39+hh, 40+hh, 41+hh, 42+hh, 31+ii, 32+ii, 33+ii, 34+ii, 35+ii, 36+ii, 37+ii, 38+ii, 39+ii, 40+ii, 41+ii, 42+ii.

Example 2

Example 2 illustrates the fact that good protective effect may be obtained by using compositions of the invention comprising a salt as defined herein, such as calcium gluconate (CG) and antagonistic yeast's active against postharvest diseases caused by moulds on fruits of *Malus* species.

Vegetal Material

Apples (*Malus domestica* Borkh cv. Golden) were harvested from commercial orchards maintained with standard cultural practices in Belgium and placed in regular long term storage. Commercial class I fruits were used. They were bought from wholesale dealers and stored in a cold room at 4±1° C. for maximum 15 days before use.

Pathogens

*Penicillium expansum* (blue mould) strains were initially isolated from apples in Gembloux Belgium. Conidia from pathogen were put in suspension in a glycerol solution (25%) and stored at −70° C. Starting from this stored material, the fungal strain was transferred to PDA medium at 25° C. Conidial suspensions were prepared in an aqueous sterile solution of Tween 20 (0.05%), and were adjusted to the required concentration ($10^6$ spores/ml) using a Bürker cell.

Antagonistic Micro-Organisms

The antagonistic yeast strain was *Candida oleophila* Montrocher deposited under number 40564 at the BBCM™/MUCL Culture Collection of the Mycothèque de l'Université Catholique de Louvain, hereinafter designated as "strain O".

This antagonistic yeast strain was isolated from apple surface and stored at −70° C. in a glycerol solution (25%). Before use, the yeast strain was subcultured three times successively at 24 hours intervals on PDA (Potato Dextrose Agar). At the third generation, yeast cells were removed from the culture medium and suspended in isotonic water (NaCl 0.85%). Suspension concentrations were adjusted to the required values after the establishment of a regression line in relation with the micro-organisms suspension absorbance (at 595 nm) and the number of colony forming units (cfu) of the same suspension spread onto PDA.

Treatment

Fruits were disinfected by dipping for 2 minutes in sodium hypochlorite (10% of the commercial product). They were rinsed in sterile water and dried out under laminar flux before being wounded by removing 4 mm diameter and 2-3 mm deep blocks of tissue from three sites 4-5 cm apart along one side of the surface of the fruits.

The wounds were treated by application of 40 µl of compositions of the state of the art or compositions according to the invention.

After a 24 h at 20° C. incubation period in plastic boxes, the wounds were inoculated with 40 µl of the respective conidial suspensions of the pathogens. The fruits were incubated at 25° C.

The diameters of the lesions developing around the wounds were measured after 7 days after inoculation of the pathogen. At least five fruits (15 wounds) were used per treatment. Most of the time, 15 fruits and 45 wounds were used per treatment.

The percentage of protection provided by the different treatments was calculated from the diameter of lesion caused by the fruit rot agent after the incubation time using the following formula:

$$\frac{D_T - D_X}{D_T} \times 100 = Y\%$$

wherein Y is the percentage of protection; $D_T$ is the mean diameter of lesions for the untreated control and $D_X$ is the mean diameter of lesions for the treated fruits.

The effect of the compositions according to the invention against postharvest apple rots caused by *P. expansum* was evaluated under controlled conditions.

In the remaining parts of the description, GC stands for Calcium Gluconate in monohydrated form (CAS Number: 299-28-5), food grade, Jungbunzlauer, Germany. CN stands for Calcium Nitrate (tetrahydrate), 98%, VWR. These products are known per se and commercially available.

In a first series of experiments, standard compositions of strain O were used as control. The standard concentration for the use of strain O is $10^7$ colony forming units per milliliter (cfu/ml), whereas the concentration of $10^5$ cfu/ml is considered as suboptimal. Indeed, it can be seen in table 3 that results (which are expressed in terms of percentage of protection calculated as defined above), obtained with this concentration when using strain O alone are not satisfactory.

TABLE 3

| | Protection against *Penicillium expansum* | | | | | |
|---|---|---|---|---|---|---|
| Strain O | Control 0 | $10^7$ | $10^5$ | $10^5$ | $10^5$ | $10^5$ |
| Calcium salt | 0 | 0 | 0 | CG 2 g/l | CN 1.2 g/l | CN 2.4 g/l |
| Average infection | 11.5 | 0.8 | 2.00 | 1.5 | 7.6 | 10.9 |
| Protection Efficiency (%) | — | 93.1 | 82.7 | 87.3 | 34.1 | 5.8 |

According to the present invention, it was surprisingly found that a composition that comprised the suboptimal concentration of $10^5$ cfu/ml of strain O and 2 g/l CG improved the protection.

Furthermore, it was found that a composition which comprised the suboptimal concentration $10^5$ cfu/ml of strain O and calcium nitrate either at 1.2 g/l or at 2.4 g/l was less efficient in protecting the fruit against *P. expansum* than a composition containing the strain O alone, or than a composition according to an embodiment of the present invention i.e. comprising the strain O with CG at 2 g/l.

In a second series of experiments on apples, results of which are given in table 4, standard compositions of strain O have been used as control.

TABLE 4

|  | Control |  |  |  |
| --- | --- | --- | --- | --- |
| Strain O | 0 | $10^7$ | $10^5$ | $10^5$ |
| CG | 0 | 0 | 0 | 2 g |
| Average infection | 12.9 | 6.1 | 8.4 | 1.2 |
| Protection Efficiency % |  | 52.6 | 35.1 | 90.7 |

In first composition, the concentration of strain O used was the standard concentration of $10^7$ cfu/ml, whereas in the second one, the concentration used was the suboptimal concentration of $10^5$ cfu/ml.

Again, it was surprisingly found that a composition that comprised the suboptimal concentration of $10^5$ cfu/ml of strain O and 2 g/l CG improved the protection of fruit against the pathogen.

In a third series of experiments on apples, results of which are given in table 5, standard compositions of strain O have been used as control.

TABLE 5

|  | Control |  |  |  |
| --- | --- | --- | --- | --- |
| Strain O | 0 | $10^7$ | $10^5$ | $10^5$ |
| CG | 0 | 0 | 0 | 2 g |
| Average infection | 13.2 | 3.7 | 7.1 | 2.7 |
| Protection Efficiency % |  | 71.7 | 46.0 | 79.3 |

According to the invention, the addition of CG allows reducing the concentration of strain O hundred fold down to $10^5$ cfu/ml while obtaining better and enhanced efficacy against *P. Expansum* than with the standard concentration of $10^7$ cfu/ml. This result illustrates the remarkable properties of the composition according to the present invention.

Example 3

Vegetal Material

Apples (*Malus domestica* Borkh cv. Golden) are as described in Example 2.

Pathogens

*Penicillium expansum* as described in Example 2

Antagonistic Micro-Organisms

The antagonistic yeast strain was *Candida oleophila* as described in Example 2.

Treatment

The apples were wounded as described in Example 2 and treated by application of compositions comprising a salt according to the invention and $10^5$ cfu *C. oleophila*, or compositions of the state of the art. The salts used were: calcium gluconate (CG), tricalcium citrate: (TC), calcium carbonate (CCa), calcium lactate (CL), calcium lactogluconate (CLG), calcium ascorbate (CA)

After incubation, the wounds were inoculated with *Penicillum expansum*. The fruits are further incubated. The diameters of the lesions developing around the wounds were measured after 7 days after inoculation of the pathogen. The percentage of protection provided by the different treatments was calculated as described in Example 2. The results of the protective effect of the combination of antagonist and salts on decay of apple from two series of experiments are shown in Tables 6a and 6b. Standard compositions of strain O ($10^7$) have been used as control.

TABLE 6a

| Strain O | Control no strain | $10^7$ | $10^5$ | $10^5$ | $10^5$ | $10^5$ | $10^5$ | $10^5$ | $10^5$ |
| --- | --- | --- | --- | --- | --- | --- | --- | --- | --- |
| Salt | | | | CG | TC | CCa | CL | CLG | CA |
| concentration | 0 | 0 | 0 | 2 g/l | 0.87 g/l | 0.47 g/l | 1.34 g/l | 1.3 g/l | 1.96 g/l |
| Average infection | 18.4 | 5.2 | 9.2 | 4.8 | 2.8 | 4.1 | 7.7 | 5.6 | 5.4 |
| Efficiency % | 0 | 71.8 | 50.3 | 73.8 | 84.8 | 77.9 | 58.1 | 69.4 | 70.9 |

TABLE 6b

| Strain O | Control no strain | $10^7$ | $10^5$ | $10^5$ | $10^5$ | $10^5$ | $10^5$ | $10^5$ | $10^5$ |
| --- | --- | --- | --- | --- | --- | --- | --- | --- | --- |
| Salt | | | | CG | TC | CCa | CL | CLG | CA |
| concentration | 0 | 0 | 0 | 2 g/l | 0.87 g/l | 0.47 g/l | 1.34 g/l | 1.3 g/l | 1.96 g/l |
| Average infection | 4.07 | 6.20 | 5.53 | 6.50 | 6.67 | 3.72 | 6.06 | 6.21 | 5.31 |
| Efficiency % | 0 | 84.3 | 67.0 | 74.2 | 83.3 | 92.8 | 82.5 | 86.3 | 86.7 |

According to the invention, the addition of the different salts allows reducing the concentration of strain O hundred fold down to $10^5$ cfu/ml and permits to obtain better protection at this concentration compared to strain O alone.

In another series of experiments on apples, results of which are given in table 7, standard compositions of strain O have been used as control, and the salts used were: calcium gluconate (CG) tricalcium citrate (TC) and calcium carbonate (CCa).

TABLE 7

| Strain O | Control no strain | $10^5$ | $10^7$ | $10^5$ | $10^5$ | $10^5$ | $10^5$ |
|---|---|---|---|---|---|---|---|
| Salt | | | | CaCl$_2$ | CG | TC | CCA |
| concentration | | | | 20 g/l | 2 g/l | 0.87 g/l | 0.47 g/l |
| Average infection | 26.5 | 6.5 | 3.4 | 0.7 | 1.7 | 1.0 | 0.7 |
| Efficiency % | | 75.5 | 87.1 | 97.4 | 93.5 | 96.4 | 97.2 |

The combination of antagonistic microorganisms with the different salts according to the invention, allows reducing the concentration of strain O hundred fold down to $10^5$ cfu/ml while obtaining better and enhanced efficacy against *P. Expansum* than with the concentration of $10^7$ cfu/ml. Additionally, the composition according to the invention allows reducing significantly the amount of salts needed when compared to prior art CaCl$_2$ amounts used to obtain equivalent protection.

Example 4

Vegetal Material

Apples (*Malus domestica* Borkh cv. Golden) are as described in Example 2.

Pathogens:
*Penicillium expansum* as described in Example 2

Antagonistic Micro-Organisms:
The antagonistic yeast strain was *Candida oleophila* as described in Example 2.

Treatment:

The apples were wounded as described in Example 2 and treated by application of compositions comprising a salt according to the invention and $10^5$ cfu *C. oleophila*, or compositions of the state of the art.

After incubation, the wounds were inoculated with *Penicillum expansum*. The fruits are further incubated. The diameters of the lesions developing around the wounds were measured after 7 days after inoculation of the pathogen. The percentage of protection provided by the different treatments was calculated as described in Example 2. The results are shown in Table 8. Standard compositions of strain O have been used as control. The salts used were: calcium gluconate (CG), calcium carbonate (CCa), calcium bicarbonate (CBC), calcium phosphate monobasic (CPM), and calcium phosphate tribasic (CPT).

TABLE 8

| Strain O | Control | $10^7$ | $10^5$ | $10^5$ | $10^5$ | $10^5$ | $10^5$ | $10^5$ | $10^5$ |
|---|---|---|---|---|---|---|---|---|---|
| Salt | | | | CaCl$_2$ | CG | CCa | CBC | CPT | CPM |
| Concentration | | | | 20 g/l | 2 g/l | 0.47 g/l | 0.762 g/l | 0.486 g/l | 1.485 g/l |
| Average infection | 2.3 | 1.0 | 1.2 | 0.3 | 0.5 | 0.3 | 0.5 | 0.4 | 0.1 |
| Efficiency % | | 55.8 | 45.4 | 87.6 | 77.4 | 88.6 | 76.5 | 84.1 | 94.4 |

In the same experiment the diameters of the lesions developing around the wounds were measured after 11 days after inoculation of the pathogen. The percentage of protection provided by the different treatments was calculated as described in Example 2. The results are shown in Table 9. Standard compositions of strain O have been used as control. The salts used were: calcium gluconate (CG), calcium carbonate (CCa), calcium bicarbonate (CBC), calcium phosphate monobasic (CPM), and calcium phosphate tribasic (CPT).

TABLE 9

| Strain O | Control | $10^7$ | $10^5$ | $10^5$ | $10^5$ | $10^5$ | $10^5$ | $10^5$ | $10^5$ |
|---|---|---|---|---|---|---|---|---|---|
| Salt | | | | CaCl$_2$ | CG | CCa | CBC | CPT | CPM |
| Concentration | | | | 20 g/l | 2 g/l | 0.47 g/l | 0.762 g/l | 0.486 g/l | 1.485 g/l |
| Average infection | 5.1 | 2.8 | 2.8 | 0.6 | 1.5 | 0.8 | 2.1 | 0.9 | 0.7 |
| Efficiency % | | 45.2 | 44.1 | 87.7 | 70.5 | 85.1 | 59.0 | 82.1 | 86.6 |

It can be seen from the results of Tables 8 and 9 that calcium gluconate, calcium carbonate, calcium bicarbonate, calcium phosphate monobasic, and calcium phosphate tribasic provides a good protection against *Penicillium expansum* when compared with the use of the antagonistic microorganism alone at the same concentration.

Example 5

Vegetal Material

Apples (Malus domestica Borkh cv. Golden) are as described in Example 2.
Pathogens:
 *Botrytis cinerea*.
Antagonistic Micro-Organisms:
 The antagonistic yeast strain was *Candida oleophila* as described in Example 2.
Treatment:
 The apples were wounded as described in Example 2 and treated by application of compositions comprising a salt according to the invention and $10^5$ cfu *C. oleophila*, or compositions of the state of the art.
 After incubation, the wounds were inoculated with *Penicillum expansum*. The fruits are further incubated. The diameters of the lesions developing around the wounds were measured after 5 days after inoculation of the pathogen. The percentage of protection provided by the different treatments was calculated as described in Example 2. The results are shown in Table 10. Standard compositions of strain O have been used as control. The salts used were: calcium gluconate (CG), tricalcium citrate: (TC), potassium citrate (PC), calcium glutamate (CGt).

TABLE 10

| Strain O | Control | $10^7$ | $10^5$ | $10^5$ | $10^5$ | $10^5$ | $10^5$ | $10^5$ |
|---|---|---|---|---|---|---|---|---|
| Salt | | | | CaCl$_2$ | CG | CGt | TC | PC |
| Concentration | | | | 20 g/l | 2 g/l | 1.805 g/l | 0.848 g/l | 0.964 g/l |
| Average infection | 1.6 | 0.3 | 0.9 | 0.3 | 0.6 | 0.8 | 0.3 | 0.5 |
| Efficiency % | | 84.2 | 43.3 | 82.4 | 60.7 | 51.3 | 78.9 | 66.4 |

CONCLUSIONS

All the results given in these examples show that the compositions according to the present invention demonstrate higher efficiency than that provided by compositions of the state of the art containing micro-organisms strains used at the same application concentration. The surprising properties of the salts as described herein on the protective properties of the antagonistic microorganism were clearly demonstrated by the present examples. Very good results have been obtained using combination of calcium gluconate, calcium citrate, potassium citrate, potassium glutamate, calcium phosphate monobasic, calcium phosphate tribasic, calcium carbonate, calcium bicarbonate, calcium ascorbate, calcium lactate or calcium lactogluconate with *C. oleophila*.

The salts used in the present invention are surprisingly good boosting compounds which allow lowering the concentration of an antagonistic micro-organism without lowering the efficiency of the compositions against pathogens. They also allow lowering the concentration of an antagonistic micro-organism while prolonging the duration of the efficiency of the composition against pathogens.

The invention claimed is:
1. A composition for use against one or more pathogens, comprising at least one *Candida oleophila* as antagonistic micro-organism and at least one salt selected from the group consisting of calcium phosphate monobasic Ca(H$_2$PO$_4$)$_2$, calcium phosphate dibasic (CaHPO$_4$), calcium phosphate tribasic (Ca$_3$(PO4)$_2$), calcium gluconate, calcium lactogluconate, calcium ascorbate, and calcium citrate, wherein the amount of the salt is between 0.005 and 5 g/l w/v and wherein said *Candida oleophila* is applied at a concentration ranging from $10^4$ to $10^8$ cfu/ml, wherein the pathogens are selected from the group consisting of *Alternaria* spp., *Ascochyta* spp., *Aspergillus* spp., *Botrytis* spp., *Cercospora* spp., *Cladosporium* spp., *Claviceps* spp., *Colletotrichum* spp., *Erysiphe* spp., *Fusarium* spp., *Geotrichum* spp., *Gilbertella* spp., *Gloeosporium* spp., *Helminthosporium* spp., *Monilia* spp., *Monilinia* spp., *Mucov* spp., *Nectria* spp., *Penicillium* spp., *Peronospora* spp., *Pezicula* spp., *Phomopsis* spp., *Phytophthora* spp., *Plasmopara* spp., *Podosphaera* spp., *Pseudocercosporium* spp., *Puccinia* spp., *Rhizoctonia* spp., *Rhizopus* spp., *Rynchosporium* spp., *Sclerotinia* spp., *Septoria* spp., *Sphaerotheca* spp., *Uncinula* spp., *Ustilago* spp., *Venturia* spp., *Verticillium* spp.
2. A method for treating diseases caused by pathogens to vegetal material comprising the step of applying a composition according to claim 1 to the vegetal material wherein the pathogens are selected from the group consisting of *Alternaria* spp., *Ascochvta* spp., *Aspergillus* spp., *Botrytis* spp., *Cercospora* spp., *Cladosporium* spp., *Claviceps* spp., *Colletotrichum* spp., *Erysiphe* spp., *Fusarium* spp., *Geotrichum* spp.,

*Gilbertella* spp., *Gloeosporium* spp., *Helminthosporium* spp., *Monilia* spp., *Monilinia* spp., *Mucov* spp., *Nectria* spp., *Penicillium* spp., *Peronospora* spp., *Pezicula* spp., *Phomopsis* spp., *Phvtophthora* spp., *Plasmopara* spp., *Podosphaera* spp., *Pseudocercosporium* spp., *Puccinia* spp., *Rhizoctonia* spp., *Rhizopus* spp., *Rynchosporium* spp., *Sclerotinia* spp., *Septoria* spp., *Sphaerotheca* spp., *Uncinula* spp., *Ustilago* spp., *Venturia* spp., *Verticillium* spp.

3. The method according to claim 2, wherein said vegetal material is selected from the group consisting of fruits of the species *Malus* spp., *Pyrus* spp. and *Citrus* spp.; crops; tropical fruit; melon fruit; and flowers and ornamental crops.

4. The method according to claim 1, wherein the pathogens are selected from the group consisting of *Alternaria alternata, Ascochyta* sp., *Aspergillus flavus, Aspergillus niger, Botrytis alii, Botrytis cinerea, Botrytis fabae, Cercospora* sp., *Cladosporium* sp., *Claviceps purpurea, Colletotrichum* sp., *Erysiphe betae, Erysiphe graminis, Fusarium oxysporum, Geotrichum candidum, Gilbertella persicovia, Gloeosporium perennans, Gloeosporium fructigenum, Helminthosporium* sp., *Monilia* sp., *Monilinia fructicola, Monilinia laxa, Mucov* sp., *Nectria cinnabarina, Penicillium digitatum, Penicillium expansum, Penicillium italicum, Peronospora* sp., *Pezicula malicorticas, Phomopsis viticola, Phytophthora infestans, Plasmopara viticola, Podosphaera leucotricha, Pseudocercosporium* sp., *Puccinia graminis, Rhizoctonia* sp., *Rhizopus arrhizus, Rhizopus stolonifer, Rynchosporium* sp., *Sclerotinia Cepivorum, Sclerotinia sclerotiorum, Septoria apicola, Sphaerotheca* sp., *Uncinula necator, Ustilago* sp., *Venturia inaequalis, Verticillium albo-atrum*, and *Verticillium dahliae*.

5. The method according to claim 2, wherein the pathogens are selected from the group consisting of *Botrytis* spp., *Penicillium* spp., *Pezicula* spp., and *Rhizopus* spp.

6. A method for treating plant material comprising simultaneous, separate or sequential administration to a plant to be treated of a composition comprising at least one *Candida oleophila* as antagonistic micro-organism and at least one salt and/or derivative thereof, wherein said salt is selected from the group consisting of calcium phosphate monobasic $Ca(H_2PO_4)_2$, calcium phosphate dibasic ($CaHPO_4$), calcium phosphate tribasic ($Ca_3(PO_4)_2$), calcium gluconate, calcium citrate, calcium lactogluconate, and calcium ascorbate, wherein the amount of the salt is between 0.005 and 5 g/l w/v and wherein said *Candida oleophila* is applied at a concentration ranging from $10^4$ to $10^8$ cfu/ml, wherein the pathogens are selected from the group consisting of *Alternaria* spp., *Ascochyta* spp., *Aspergillus* spp., *Botrytis* spp., *Cercospora* spp., *Cladosporium* spp., *Claviceps* spp., *Colletotrichum* spp., *Erysiphe* spp., *Fusarium* spp., *Geotrichum* spp., *Gilbertella* spp., *Gloeosporium* spp., *Helminthosporium* spp., *Monilia* spp., *Monilinia* spp., *Mucov* spp., *Nectria* spp., *Penicillium* spp., *Peronospora* spp., *Pezicula* spp., *Phomopsis* spp., *Phytophthora* spp., *Plasmopara* spp., *Podosphaera* spp., *Pseudocercosporium* spp., *Puccinia* spp., *Rhizoctonia* spp., *Rhizopus* spp., *Rynchosporium* spp., *Sclerotinia* spp., *Septoria* spp., *Sphaerotheca* spp., *Uncinula* spp., *Ustilago* spp., *Venturia* spp., *Verticillium* spp.

7. A method for the biocontrol of diseases caused by pathogens to vegetal material, comprising the step of applying a composition as defined in claim 1 to said vegetal material wherein the pathogens are selected from the group consisting of *Alternaria* spp., *Ascochvta* spp., *Aspergillums* spp., *Botrytis* spp., *Cercospora* spp., *Cladosporium* spp., *Claviceps* spp., *Colletotrichum* spp., *Erysiphe* spp., *Fusarium* spp., *Geotrichum* spp., *Gilbertella* spp., *Gloeosporium* spp., *Helminthosporium* spp., *Monilia* spp., *Monilinia* spp., *Mucov* spp., *Nectria* spp., *Penicillium* spp., *Peronospora* spp., *Pezicula* spp., *Phomopsis* spp., *Phvtophthora* spp., *Plasmopara* spp., *Podosphaera* spp., *Pseudocercosporium* spp., *Puccinia* spp., *Rhizoctonia* spp., *Rhizopus* spp., *Rynchosporium* spp., *Sclerotinia* spp., *Septoria* spp., *Sphaerotheca* spp., *Uncinula* spp., *Ustilago* spp., *Venturia* spp., *Verticillium* spp.

8. A method for the manufacture of a composition as defined in claim 1 comprising the step of mixing at least one *Candida oleophila* with at least one salt and/or derivative thereof.

9. A method for enhancing the efficacy of a composition comprising at least one *Candida oleophila* as antagonistic microorganism, said method comprising the step of adding at least one salt to the composition, wherein said salt is selected from the group consisting of calcium phosphate monobasic $Ca(H_2PO_4)_2$, calcium phosphate dibasic ($CaHPO_4$), calcium phosphate tribasic ($Ca_3(PO4)_2$), calcium gluconate, calcium citrate, calcium lactogluconate, and calcium ascorbate, wherein the amount of the salt is between 0.005 and 5 g/l w/v and wherein said *Candida oleophila* is applied at a concentration ranging from $10^4$ to $10^8$ cfu/ml, wherein the pathogens are selected from the group consisting of *Alternaria* spp., *Ascochyta* spp., *Aspergillus* spp., *Botrytis* spp., *Cercospora* spp., *Cladosporium* spp., *Claviceps* spp., *Colletotrichum* spp., *Erysiphe* spp., *Fusarium* spp., *Geotrichum* spp., *Gilbertella* spp., *Gloeosporium* spp., *Helminthosporium* spp., *Monilia* spp., *Monilinia* spp., *Mucov* spp., *Nectria* spp., *Penicillium* spp., *Peronospora* spp., *Pezicula* spp., *Phomopsis* spp., *Phytophthora* spp., *Plasmopara* spp., *Podosphaera* spp., *Pseudocercosporium* spp., *Puccinia* spp., *Rhizoctonia* spp., *Rhizopus* spp., *Rynchosporium* spp., *Sclerotinia* spp., *Septoria* spp., *Sphaerotheca* spp., *Uncinula* spp., *Ustilago* spp., *Venturia* spp., *Verticillium* spp.

10. The composition according to claim 1, wherein the amount of the salt is between 0.01 and 4 g/l w/v.

11. The composition according to claim 1, wherein the amount of the salt is between 0.1 and 3 g/l w/v.

12. The composition according to claim 1, wherein the amount of the salt is between 0.01 and 2.5 g/l w/v.

13. The composition according to claim 1, wherein the amount of the salt is between 0.1 and 2.2 g/l w/v.

14. The method according to claim 3, wherein said vegetal material is a fruit of the species *Malus* spp. *Pyrus* spp., *Citrus* spp. selected from the group consisting of oranges, lemons, grapefruits and tangerines.

15. The method according to claim 3, wherein the vegetal material is a crop of the species selected from the group consisting of tomatoes, bell peppers, cucumbers, grapevines and strawberries.

16. The method according to claim 3, wherein the vegetal material is a root crop selected from the group consisting of potatoes and carrots.

17. The method according to claim 3, wherein the vegetal material is a tropical fruit selected from the group consisting of mangos, bananas, guavas, pineapples and avacados.

18. The composition according to claim 1, wherein the pathogens are selected from the group consisting of *Alternaria* spp., *Aspergillus* spp., *Botrytis* spp., *Colletotrichum* spp., *Fusarium* spp., *Geotrichum* spp., *Gloeosporium* spp., *Monilia* spp., *Penicillium* spp., *Pezicula* spp., *Phytophthora* spp., *Plasmopara* spp., *Podosphaera* spp., *Rhizoctonia* spp., *Rhizopus* spp., *Sclerotinia* spp., *Uncinula* spp., *Ustilago* spp., *Venturia* spp., *Verticillium* spp.

19. The composition according to claim 1, wherein the pathogens are selected from the group consisting of *Botrytis* spp., *Colletotrichum* spp., *Monilia* spp., *Penicillium* spp., *Pezicula* spp., *Phytophthora* spp., *Sclerotinia* spp., *Uncinula* spp., *Venturia* spp.

\* \* \* \* \*